United States Patent [19]

Winicov et al.

[11] 4,048,336

[45] Sept. 13, 1977

[54] MEANS FOR KILLING BACTERIAL SPORES WITH GLUTARALDEHYDE SPORICIDAL COMPOSITIONS

[75] Inventors: Murray A. Winicov, Flushing, N.Y.; Abraham Cantor, Elkins Park, Pa.

[73] Assignee: West Chemical Products, Incorporated, Long Island City, N.Y.

[21] Appl. No.: 570,638

[22] Filed: Apr. 23, 1975

Related U.S. Application Data

[60] Continuation of Ser. No. 463,200, April 22, 1974, abandoned, which is a division of Ser. No. 157,681, June 28, 1971, abandoned.

[51] Int. Cl.$^2$ ............................................. A01N 9/24
[52] U.S. Cl. ................................... 424/334; 424/333
[58] Field of Search ............................... 424/333, 334

[56] References Cited

U.S. PATENT DOCUMENTS

| | | | |
|---|---|---|---|
| 2,801,216 | 7/1957 | Yoder et al. | 424/333 |
| 3,016,328 | 1/1962 | Pepper et al. | 424/127 |
| 3,057,775 | 10/1962 | Rendon | 424/75 |
| 3,282,775 | 11/1966 | Stonehill | 424/263 |
| 3,503,885 | 3/1970 | Wedell | 252/106 |
| 3,650,964 | 3/1972 | Sedliar et al. | 252/106 |
| 3,666,668 | 4/1972 | Klausner | 252/106 |
| 3,697,222 | 10/1972 | Sierra | 21/58 |
| 3,912,450 | 10/1975 | Boucher | 21/54 A |

OTHER PUBLICATIONS

J. of Pharm. Sci. 53(10) pp. 1273-1275 (1964) – Borick et al. "Alkalinized Glutaraldehyde-Agent".
Currents in Mod. Biology 1 pp. 14-20 (1967) – Egyud – "Studies on Cell Division... ".
Chem. Abst. 65 5686(c), 1966 – "Disinfection of Textiles" Boehne Fettchemie.

*Primary Examiner*—Albert T. Meyers
*Assistant Examiner*—D. W. Robinson
*Attorney, Agent, or Firm*—Howard E. Thompson, Jr.

[57] ABSTRACT

This invention relates to new and improved means for killing spores on instruments and the like utilizing the combination of glutaraldehyde and a monoaldehyde, such as, for example, formaldehyde. The sporicidal kill activity of the composition is more rapid than previously possible, and more effective than the use of either glutaraldehyde or monoaldehyde alone.

17 Claims, No Drawings

MEANS FOR KILLING BACTERIAL SPORES WITH GLUTARALDEHYDE SPORICIDAL COMPOSITIONS

CROSS REFERENCE TO RELATED APPLICATIONS

This application is a continuation of U.S. Ser. No. 463,200, filed Apr. 22, 1974, which in turn is a divisional of U.S. Ser. No. 157,681, filed June 28, 1971, all by the present inventors. Both these applications are now abandoned.

BACKGROUND OF THE INVENTION

The prior art is replete with a variety of compositions directed toward the effective killing of bacterial spores. Among the most important developments in this area are the compositions disclosed in U.S. Pat. No. 3,016,328 to Pepper et al and U.S. Pat. No. 3,282,775 to Stonehill. In the former patent saturated dialdehydes provide sporicidal activity and the pH of the composition is controlled so that it is maintained in excess of 7.4 by including an alkalinizing agent. The sporicidal composition disclosed in the latter patent to Stonehill is also characterized as containing a saturated dialdehyde, including cationic surface active agents. In the Stonehill patent, it is expressly stated that anionic and/or nonionic detergents do not increase the sporicidal activity of the compositions.

While the patent to Pepper et al limits the pH of the sporicidal composition to a minimum in excess of at least 7.4, the Stonehill patent discloses no such limitation as the compositions disclosed therein are stated to be effective over a wide pH range of 4.0–9.0.

Each of the sporicidal compositions disclosed in the above-identified patents claim very fast sporicidal action of about 3 hours or less. However, close examination of the conditions upon which such fast kill claims were determined reveals that the "kills" were obtained against readily susceptible bacterial spores and that neither patent discloses any sporicidal activity results for bacterial spores on silk sutures, which carrier is specified as being required by the AOAC test procedure. Furthermore, it is well known that resistance of bacterial spores to chemical sterilizing agents is lowest in free suspension, intermediate on porcelain rings and most resistant on silk sutures. Recently, the claims for sporicidal compositions marketed by the common assignee of the above-noted patents had to be revised in their registration with the USDA from a contact kill time of 3 hours upward to 10 hours.

Independent analyses of the sporicidal compositions disclosed in U.S. Pat. No. 3,016,328 to Pepper et al revealed that the 10 hour contact kill time was readily obtainable when using a fresh solution, but that the efficacy of the compositions markedly decreased upon standing for prolonged periods of up to about 2 weeks. Further, this reduction in effectiveness was found to be attributable to the diminution of glutaraldehyde, which lost a total of about 25% of its value by the end of a two week period.

It can be seen, therefore, that these two principal disclosures relating to sporicidal compositions, under the limited test conditions set forth therein may not, in reality, exhibit the effectiveness implied for them with respect to passing the complete AOAC test. Furthermore, the effectiveness of the disclosed compositions are based upon those bacterial spores and/or carriers which are known to favor relatively easy "kills."

It has now been found that the shortcomings of the prior art can be overcome by use of the glutaraldehyde sporicidal compositions of the invention which employ the combination of glutaraldehyde and monoaldehyde, such as formaldehyde. The compositions provide a minimum amount of glutaraldehyde in a suitable sporicidal solvent and may further include an anionic, nonionic, cationic or ampholytic detergent therein to obtain enhanced sporicidal activity. Further, by closely controlling the pH of the compositions, significantly improved shelf life is provided which is manifested by the sporicidal performance of the activated compositions, even after standing for prolonged periods of 2 to 3 weeks.

The amount of glutaraldehyde incorporated in the sporicidal solvent should be no less than about 0.5% by weight, since lesser amounts unduly prolong the kill times, while the maximum amount which can be used is essentially without limit. The term "sporicidal solvent," as used throughout this application and in the claims, should be understood as referring to those solvents normally employed for sporicidal compositions and which include water and/or alcohols. For example, the U.S. Patents to Pepper et al and Stonehill et al discussed above, each disclose the use of alcohols as a sporicidal solvent. However, in this invention, water is the preferred sporicidal solvent to be used, although other sporicidal solvents can also be employed.

The addition of activating agents to adjust the pH of sporicidal compositions is well known to those skilled in the art. Generally, glutaraldehyde compositions are stable almost indefinitely within the pH range of about 2.5–4.5 at which pH levels they are stored before use. Just prior to use, their pH levels are adjusted through the addition of activating agents. Hence, most sporicidal compositions are made commercially available as a two package system, one of which comprises the sporicide in a suitable solvent and the other of which contains the activating agent, either as a powder or in solution, which is to be added to the sporicidal composition to activate it and adjust its pH just prior to use. The addition of such agents has been noted above in discussing the patent to Pepper et al (U.S. Pat. No. 3,016,328) wherein this procedure is referred to as "alkalinizing" the composition. In the context of this invention, the term "activating" is employed and should be understood to be equivalent to alkalinizing such compositions and adjusting their pH levels by adding well known buffering agents to them. Once activated in this manner, the sporicidal compositions of the prior art have been found to have limited shelf lives and are, therefore, generally utilized immediately, or within a very short time, after being activated. It is to this particular problem that one embodiment of this invention is directed for it has now been found that upon activating the sporicidal compositions of this invention so that their pH levels are maintained within a specified range, improved shelf life stability can be obtained.

The pH of the activated sporicidal compositions of the invention can be controlled by incorporating therein one or more of the suitable and well known buffering agents so that the pH of the composition is no greater than 7.4, preferably about 6.5 to 7.4, and optimumly at a pH of 7.0 ± 0.3. The selection of suitable buffering agents for controlling the pH level is not critical and such materials as phosphates, citrates, carbonates, bicarbonates and the like, can be readily employed, although the phosphates are particularly preferred due to their favorable dissociation constants. As is well known in the art, other ingredients such as anti-corrosion agents, dyes, and the like, can also be added to the compositions.

In the principal embodiment of the invention it has been found that the inclusion of one or more monoaldehydes results in a synergistic effect of greatly reduced kill times thereby further enhancing the efficacy of the composition. Such compositions are especially effective for killing *Bacillus subtilis* (*B. subtilis*), one of the acknowledged most difficult bacterial spores to kill. The monoaldehydes should be present in amounts no less than about 0.5% with the upper amounts being limited only by their solubility in the sporicidal solvent being employed. Illustrative of the monoaldehydes which can be employed are formaldehyde, acetaldehyde, propionaldehyde, and butyraldehyde, formaldehyde being preferred.

The detergents which can additionally be employed in the composition are not limited to any one of the known detergent classes or groups, and it has been found that their use serves to potentiate; that is, increase and enhance, the sporicidal activity of the compositions. The minimum amount of detergent which should be employed is about 0.01% by weight with a range of about 0.1 to 1.0% preferred. For the purposes of this invention the term "detergent" should be understood as referring to any substance which, when added to water at a concentration of 0.1%, will depress the surface tension of water by at least 20 dynes per square centimeter. Under this criterion, any nonionic, anionic, cationic, and/or ampholytic detergents can be utilized. When exposed to some materials, such as metal instruments; for example, scalpels, anionic detergents may exhibit a corrosive effect, and for this reason the nonionic detergents are preferred. Exemplary of the nonionic detergents which can be employed are the alkylphenolethoxylates available uner the Trademark "Igepal."

The sporicidal compositions of the invention have been found to be effective in killing a wide range of bacterial spores such as *Clostridium welchii* (*Cl. welchii*), *Clostridium tetani* (*Cl. tetani*), *Bacillus subtilis* (*B. subtilis*), *Bacillus pumilus* (*B. pumilus*), *Bacillus globigii* (*B. globigii*), *Clostridium sporogenes* (*Cl. sporogenes*), and the like. Of these, the *Cl. sporogenes* and the *B. subtilis* are known to be among the most difficult bacterial spores to kill, and are the organisms specified in the AOAC test.

The invention will be more fully understood when considered in light of the following examples which are set forth as being merely illustrative of the invention and are not intended to be limitative thereof. Unless otherwise indicated, all parts and percentages are by weight. The sporicidal data presented in the examples was, in all instances, obtained according to the USDA approved sporicidal test method set forth on pages 64 and 65 of the A.O.A.C., 11th edition (1970).

In the examples, the preferred detergents employed are identified by letters and/or numerals and are described in the following tabulation according to their commercial Trademarks, where applicable, and their general chemical composition. However, as previously indicated, it should be understood that while the following list sets forth preferred detergents, they are, in a broad sense, only exemplary of the entire class of nonionic, anionic, cationic, and/or ampholytic detergents which can be employed.

TABLE I

| Identification | Trademark | Type and Composition |
|---|---|---|
| IGP | "Igepal CO 710" | Nonionic—consisting essentially of nonyl phenol condensed with 10–11 mols of ethylene oxide. |
| P 65 | "Pluronic P 65" | Nonionic—consisting essentially of hydrophilic polyoxyethylene groups and a hydrophobic polyoxypropylene group; Av. M.W.-3500; 50% EO. |
| P 123 | "Pluronic P 123" | Nonionic—same general chemical composition as P 65; Av. M.W.-5650; 30% EO. |
| T-XD | "Tergitol XD" | Nonionic—a butoxy derivative of a propylene oxide-ethylene oxide block polymer. |
| $C_{12}A + 8$ EO | | Nonionic—$C_{12}$ alkanol + 8 ethylene oxide groups. |
| $C_{14}A + 10$ EO | | Nonionic—$C_{14}$ alkanol + 10 ethylene oxide groups. |
| $C_{12}A + 3$ EO-S | | Anionic—$C_{12}$ alkanol + 3 sulfated ethylene oxide groups. |
| LAS | | Anionic—linear alkane sulfonate. |
| SLS | | Anionic—sodium lauryl sulfate. |
| FC-128 | "FC-128" | Anionic—fluorinated. |
| CAT | | Cationic—cetylpyridinium chloride. |
| AMPH | "Deriphat 160" | Ampholytic—disodium N-lauryl B-imino-dipropionate. |

EXAMPLE 1

It has been found that a synergistic effect can be obtained in glutaraldehyde sporicidal composition when one or more monoaldehydes are added. To illustrate this synergistic effect, samples of sporicidal compositions were prepared in which the pH level was maintained constant at pH 7.0 and in which different detergents were either included in the amounts shown or were not included at all. The glutaraldehyde content of the compositions was varied from 2% to 4% and the amount of monoaldehyde added was also varied over a range of 0% to 6%. Since formaldehyde is the most important sporicidal monoaldehyde, it was selected to demonstrate the synergistic effect obtained. Furthermore, it is known that in order to obtain a sporicidal activity about equivalent to that when using 2% glutaraldehyde, about 10% formaldehyde would be needed. Hence, a good comparative basis was provided between the use of only glutaraldehyde and the use of only formaldehyde, although it was also found that the other higher monoaldehydes such as acetaldehyde, propionaldehyde, and butyraldehyde yielded similar results. The prepared sporicidal compositions were subjected to the above-identified AOAC test against *B. subtilis* on silk suture loops over a period of 10 hours and the results obtained are set forth below in Table II wherein glutaraldehyde is identified by the term "GLU" and formaldehyde is identified by its chemical abbreviation "HCHO". In Table II the results are shown on a "pass" or "fail" basis respectively indicated by the letter "P", which denotes no growth in any of 10 tubes, and the letter "F", which denotes 1 to 10 tubes having bacterial growth in a set of 10 tubes.

TABLE II

Synergistic Effect of Formaldehyde with Glutaraldehyde

| Sample No. | % GLU | HCHO | Det. Type | Amt. (%) | 2 hrs. | 3 hrs. | 4 hrs. | 6 hrs. | 8 hrs. | 9 hrs. | 10 hrs. |
|---|---|---|---|---|---|---|---|---|---|---|---|
| 29 | 2 | 0 | — | 0 | F | F | F | F | F | F | P |
| 30 | 2 | 1 | — | 0 | F | F | F | F | P | P | P |
| 31 | 2 | 3 | — | 0 | F | F | P | P | P | P | P |
| 32 | 4 | 0 | — | 0 | F | F | F | F | P | P | P |
| 33 | 4 | 3 | — | 0 | F | P | P | P | P | P | P |
| 34 | 2 | 0 | IGP | 1 | F | F | F | F | F | P | P |
| 35 | 2 | 3 | " | 1 | F | F | P | P | P | P | P |
| 36 | 2 | 6 | " | 1 | F | P | P | P | P | P | P |
| 37 | 4 | 0 | " | 1 | F | F | F | P | P | P | P |
| 38 | 4 | 3 | " | 1 | F | P | P | P | P | P | P |
| 39 | 2 | 1 | LAS | 5 | F | F | F | P | P | P | P |
| 40 | 4 | 3 | LAS | 1 | F | P | P | P | P | P | P |
| 41 | 2 | 1 | CAT | 1 | F | F | F | P | P | P | P |
| 42 | 2 | 6 | CAT | 0.1 | F | F | P | P | P | P | P |
| 43 | 4 | 3 | CAT | 5 | F | P | P | P | P | P | P |
| 44 | 2 | 3 | AMPH | 1 | F | F | P | P | P | P | P |

As can be seen from the above results, increasing the glutaraldehyde concentration from 2% to 4% decreases the sporicidal performance time of the composition from 10 hours to about 8 hours. However, when only 3% formaldehyde was added to the 2% glutaraldehyde, its sporicidal performance time was decreased from 10 to 4 hours. In this regard, it is significant to note that essentially the same results are obtained regardless of the type of detergent used; that is, nonionic, anionic, cationic or ampholytic detergent.

In other, similar tests conducted over a pH range of about 1 to 9, the synergistic effect illustrated in Example I was found to function at each pH level over this entire pH range. Similar synergistic results were also obtained when formaldehyde at concentrations of about 0.5 to 10% were combined with glutaraldehyde at concentrations of about 0.5 to 6%. However, the most effective synergism was found to be obtained with formaldehyde concentrations of about 1 to 6% in combination with glutaraldehyde concentrations of about 2 to 4% and these concentration ranges are preferred.

EXAMPLE 2

In order to further demonstrate the improved sporicidal performance of the compositions of the invention, a sporicidal composition was provided from one gallon of stock solution containing 4% glutaraldehyde, 3% formaldehyde and 1% of a nonionic detergent (IGP). The pH of the stock solution was adjusted to pH 4 by adding a few drops of phosphoric acid. Thereafter, this stock solution was activated by adding 16 grams of a mixture of di- and trisodium phosphate and sodium carbonate to provide a pH of 7.1. Following the normal practice in the art, incidental amounts of sodium nitrite as a corrosion inhibitor and incidental amounts of D and C Green No. 8 as a dye were also included in the activating salt mixture.

The activated solution passed the A.O.A.C. Sporicidal Test against B. subtilis and Cl. sporogenes on suture carriers within 3 hours and 2 hours, respectively, and passed the same test against both of these organisms on porcelain cylinders within even shorter time periods.

After storage for 3 weeks at room temperature (20°-25° C.), the same activated solution passed the same A.O.A.C. test against the same two spore types and test carriers (a total of four test conditions) within a maximum interval of 5 hours.

Upon further testing, this activated solution was found to also successfully sterilize bronchoscopes, cystoscopes, rubber tubing and scalpels upon immersion of these materials for a period of 5 hours.

It can be seen from the above that the present invention is an improvement over the prior art. For example, it has been demonstrated in Examples 1 and 2 that faster kills can be obtained by the combination of glutaraldehyde and monoaldehyde and that the sporicidal compositions of the invention exhibit sporicidal activity over prolonged periods. Furthermore, Example 1 illustrates that the detergents which can be employed need not be limited to the cationic group as disclosed in the patent to Stonehill et al (U.S. Pat. No. 3,282,775), but can be any detergent selected from the nonionic, anionic or ampholytic groups, provided, however, that the surface tension of the detergent selected meets the criteria set forther hereinabove.

What is claimed is:

1. A process for killing bacterial spores on instruments, appliances, eating utensils, walls, floors, and beds which comprises treating same with a sporicidally effective amount of a sporicidal composition comprising:
   a. a solvent consisting of water
   b. 0.5 to 6% by weight glutaraldehyde, and
   c. 0.5 to 10% by weight monoaldehyde, said monoaldehyde being selected from the group consisting of formaldehyde, acetaldehyde and propionaldehyde, and said composition being further characterized as having a pH no less than 6.5 and no greater than 7.4.

2. The process of claim 1 wherein said monoaldehyde is formaldehyde.

3. The process of claim 1 wherein the pH of said sporicidal composition is initially pH 7.0 ± 0.3.

4. The process of claim 1 wherein said sporicidal composition contains 2 to 4% glutaraldehyde and 1 to 6% of formaldehyde.

5. The process of claim 1 wherein said composition contains, as a fourth component (d), at least 0.1 weight % of a detergent selected from the group consisting of nonionic, anionic, cationic and ampholytic detergents.

6. The process of claim 5 wherein the amount of said detergent is 0.1 to 1 weight %.

7. A sporicidal composition for treating instruments, consisting essentially of:
   a. a solvent consisting of water
   b. 0.5 to 6% by weight glutaraldehyde, and
   c. 0.5 to 10% weight monoaldehyde, said monoaldehyde being selected from the group consisting of formaldehyde, acetaldehyde and propionaldehyde, and said composition being further characterized as having a pH no less than 6.5 and no greater than 7.4.

8. The sporicidal composition of claim 7 wherein said monoaldehyde is formaldehyde.

9. The sporicidal composition of claim 7 wherein the pH of said sporicidal composition is initially pH 7.0 ± 0.3.

10. The sporicidal composition of claim 7 which contains 2 to 4% glutaraldehyde and 1 to 6% formaldehyde.

11. The sporicidal composition of claim 7 which contains 2 to 4% glutaraldehyde and 1 to 6% of said monoaldehyde.

12. The sporicidal composition of claim 7, containing as a fourth component d. at least 0.1 weight % of a detergent selected from the group consisting of nonionic, anionic, cationic and ampholytic detergents.

13. The composition of claim 12 which contains 0.1 to 1 weight % of said detergent.

14. The sporicidal composition of claim 12 wherein said monoaldehyde is formaldehyde.

15. The sporicidal composition of claim 12 wherein the pH of said sporicidal composition is initially pH 7.0 ± 0.3.

16. The sporicidal composition of claim 12 which contains 2 to 4% glutaraldehyde and 1 to 6% formaldehyde.

17. The sporicidal composition of claim 12 which contains 2 to 4% glutaraldehyde and 1 to 6% of said monoaldehyde.

* * * * *